(12) United States Patent
Jimenez

(10) Patent No.: US 8,617,046 B2
(45) Date of Patent: Dec. 31, 2013

(54) FLOATING SLING FOR TREATMENT OF INCONTINENCE

(75) Inventor: José William Jimenez, Apple Valley, MN (US)

(73) Assignee: AMS Research Corporation, Minnetonka, MN (US)

( * ) Notice: Subject to any disclaimer, the term of this patent is extended or adjusted under 35 U.S.C. 154(b) by 846 days.

(21) Appl. No.: 11/766,202

(22) Filed: Jun. 21, 2007

(65) Prior Publication Data

US 2008/0045782 A1  Feb. 21, 2008

Related U.S. Application Data

(60) Provisional application No. 60/805,810, filed on Jun. 26, 2006.

(51) Int. Cl.
*A61F 2/02* (2006.01)

(52) U.S. Cl.
USPC .............................. 600/30; 600/37; 606/151

(58) Field of Classification Search
USPC .............. 600/29–32, 37; 128/885; 623/14.13; 606/151
See application file for complete search history.

(56) References Cited

U.S. PATENT DOCUMENTS

| | | |
|---|---|---|
| 5,112,344 A | 5/1992 | Petros |
| 5,611,515 A | 3/1997 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 6,039,686 A | 3/2000 | Kovac |
| 6,042,534 A | 3/2000 | Gellman et al. |
| 6,110,101 A | 8/2000 | Tihon et al. |
| 6,575,897 B1 * | 6/2003 | Ory et al. .................... 600/30 |
| 6,612,977 B2 | 9/2003 | Staskin et al. |
| 6,652,450 B2 | 11/2003 | Neisz et al. |
| 6,802,807 B2 | 10/2004 | Anderson et al. |
| 6,911,003 B2 | 6/2005 | Anderson et al. |
| 2002/0099259 A1 * | 7/2002 | Anderson et al. ............... 600/29 |
| 2002/0161382 A1 | 10/2002 | Neisz et al. |
| 2004/0039453 A1 | 2/2004 | Anderson et al. |
| 2005/0004427 A1 * | 1/2005 | Cervigni .................... 600/37 |
| 2005/0142163 A1 * | 6/2005 | Hunter et al. ................. 424/423 |
| 2006/0265042 A1 * | 11/2006 | Catanese et al. ............. 623/1.11 |

FOREIGN PATENT DOCUMENTS

WO    WO 03/086205    * 10/2003

OTHER PUBLICATIONS

Hackett, George S., *Ligament and Tendon Relaxation Treated by Prolotherapy*, 3d ed., Springfield, Ill., Thomas [1958].

Yamana, Tetsuo, M.D., et al., "Perineal Puborectalis Sling Operation for Fecal Incontinence: Preliminary Report," Dis. Colon Rectum, Nov. 2004; 47(11), 1982-1989.

* cited by examiner

*Primary Examiner* — Charles A Marmor, II
*Assistant Examiner* — Carrie R Dorna
(74) *Attorney, Agent, or Firm* — Gregory L. Koeller

(57) ABSTRACT

Improved methods and apparatuses for treatment of fecal and urinary incontinence are provided. Methods of placing mesh support strips adjacent the urethra or rectum (as in positions of support for levator ani muscles) through minimal number of incisions, with minimal amount of mesh, are disclosed. Methods combining such mesh support strip placement with injecting proliferative agents for support are disclosed.

8 Claims, 5 Drawing Sheets

FLOATING SLING FOR TREATMENT OF INCONTINENCE

CROSS REFERENCE TO RELATED APPLICATIONS

The present application claims the benefit of U.S. Provisional Application No. 60/805,810, filed Jun. 26, 2006, the entire disclosure of which is incorporated herein by reference.

BACKGROUND OF THE INVENTION

1. Field of the Invention

This invention relates to urogenital medicine and surgery.

2. Description of the Related Art

Over 13 million American men and women of all ages suffer from urinary and fecal incontinence. The social implications for an incontinent patient include loss of self-esteem, embarrassment, restriction of social and sexual activities, isolation, depression and, in some instances, dependence on caregivers. Incontinence is the most common reason for institutionalization of the elderly.

The urinary system consists of the kidneys, ureters, bladder and urethra. The bladder is a hollow, muscular, balloon-shaped sac that serves as a storage container for urine. The bladder is located behind the pubic bone and is protected by the pelvis. Ligaments hold the bladder in place and connect it to the pelvis and other tissue. FIG. 1 schematically illustrates the female anatomy. The urethra 16 is the tube that passes urine from the bladder 14 out of the body. The narrow, internal opening of the urethra 16 within the bladder 14 is the bladder neck 18. In this region, the bladder's bundled muscular fibers transition into a sphincteric striated muscle called the internal sphincter. FIG. 2 schematically illustrates the male anatomy. The urethra 16 extends from the bladder neck 18 to the end of the penis 22. The male urethra 16 is composed of three portions: the prostatic, bulbar and pendulus portions. The prostatic portion is the widest part of the tube, which passes through the prostate gland 24. FIG. 3 is a schematic view of the anatomy of the anus and rectum. The rectum 1 is the most distal portion of the gastrointestinal tract. The exterior opening of the rectum is the anus 2. Fecal continence is related to control of the exterior sphincter 3 and interior sphincter 4 of the anus.

Incontinence may occur when the muscles of the urinary system malfunction or are weakened. Other factors, such as trauma to the urethral area, neurological injury, hormonal imbalance or medication side-effects, may also cause or contribute to incontinence. There are five basic types of incontinence: stress incontinence, urge incontinence, mixed incontinence, overflow incontinence, and functional incontinence. Stress urinary incontinence (SUI) is the involuntary loss of urine that occurs due to sudden increases in intra-abdominal pressure resulting from activities such as coughing, sneezing, lifting, straining, exercise and, in severe cases, even simply changing body position. Urge incontinence, also termed "hyperactive bladder" "frequency/urgency syndrome" or "irritable bladder," occurs when an individual experiences the immediate need to urinate and loses bladder control before reaching the toilet. Mixed incontinence is the most common form of urinary incontinence. Inappropriate bladder contractions and weakened sphincter muscles usually cause this type of incontinence. Mixed incontinence is a combination of the symptoms for both stress and urge incontinence. Overflow incontinence is a constant dripping or leakage of urine caused by an overfilled bladder. Functional incontinence results when a person has difficulty moving from one place to another. It is generally caused by factors outside the lower urinary tract, such as deficits in physical function and/or cognitive function.

Stress urinary incontinence is generally thought to be related to hypermobility of the bladder neck or an intrinsic urethral sphincter defect.

A variety of treatment options are currently available to treat incontinence. Some of these treatment options include external devices, behavioral therapy (such as biofeedback, electrical stimulation, or Kegal exercises), injectable materials, prosthetic devices and/or surgery. Depending on age, medical condition, and personal preference, surgical procedures can be used to completely restore continence.

Conservative management of stress urinary incontinence can include lifestyle changes, such as weight loss, smoking cessation, and modification of intake of diuretic fluids such as coffee and alcohol. With regard to surgical treatments, the purported "gold standard" is the Burch Colposuspension, in which the bladder neck is suspended. Mid-urethral slings have been similarly effective. One type of procedure, found to be an especially successful treatment option for SUI in both men and women, is a sling procedure.

A sling procedure is a surgical method involving the placement of a sling to stabilize or support the bladder neck or urethra. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686; 6,042,534, 6,110,101, 6,911,003, and 6,652,450, all of which are herein incorporated by reference.

Although serious complications associated with sling procedures are infrequent, they do occur. Complications include urethral obstruction, development of de novo urge incontinence, hemorrhage, prolonged urinary retention, infection, and damage to surrounding tissue and sling erosion.

As noted above, injectable materials are an option for treatment of stress urinary incontinence. These have generally consisted of the injection of bulking agents into tissues surrounding the urethra to allow these tissues to better support the urethra, and help the urethral sphincter function properly. Collagen is sometimes used. Carbon coated beads are also used. Certain polymers have also been used. All of these injectable agents have the disadvantage of requiring multiple repeated treatments to maintain efficacy and the potential migration of these agents.

Prolotherapy is a technique wherein sclerosing substances, such as dextrose, are injected into musculosketal structures to induce changes in the ligaments and tendons due to increased proliferation of the tissue. This technique is also used in treatment of ocular conditions. In these techniques, the substance is injected. This leads to localized inflammation, which leads to the wound healing process. This results in a deposition of new collagen, which shrinks as it heals. The shrinking collagen tightens the ligaments. These techniques have not been applied to urologic disorders. These techniques are further described *Ligament and Tendon Relaxation Treated by Prolotherapy*, by George S. Hackett, which is herein incorporated by reference in its entirety.

Fecal incontinence, like urinary incontinence, has proven to be challenging to treat. Patients whose fecal incontinence is caused by external anal sphincter injury is treated successfully surgically, as with a sphincteroplasty. Other patients, though, are considered to have neurogenic or idiopathic fecal incontinence, and efforts to treat these patients has been less successful. Various procedures, such as postanal repair, total pelvic floor repair, muscle transposition techniques, dynamic gracilopasty, artificial sphincter procedures, and sacral nerve stimulation. Success has been limited, and the various treatment modalities often result in significant morbidity.

There is a desire for a minimally invasive yet highly effective treatment modality that can be used with minimal to no side effects for the treatment of both urinary and fecal incontinence. Such a modality should reduce the complexity of a treatment procedure, be biocompatible, should reduce pain, operative risks, infections and post operative hospital stays, and have a good duration of activity. Further, the method of treatment should also improve the quality of life for patients.

SUMMARY OF THE INVENTION

The present invention includes surgical instruments, implantable articles, and methods for urological applications, particularly for the treatment of stress and/or urge urinary incontinence, fecal incontinence, and prolapse and perineal floor repairs.

As noted, the usual treatments for stress urinary incontinence include placing a sling to either compress the urethral sphincter or to elevate or support the neck of the bladder defects. The present invention is a method of treating urinary and fecal incontinence in both males and females using a minimal amount of mesh material and fewer incisions. Using less mesh and fewer incisions should result in fewer complications.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
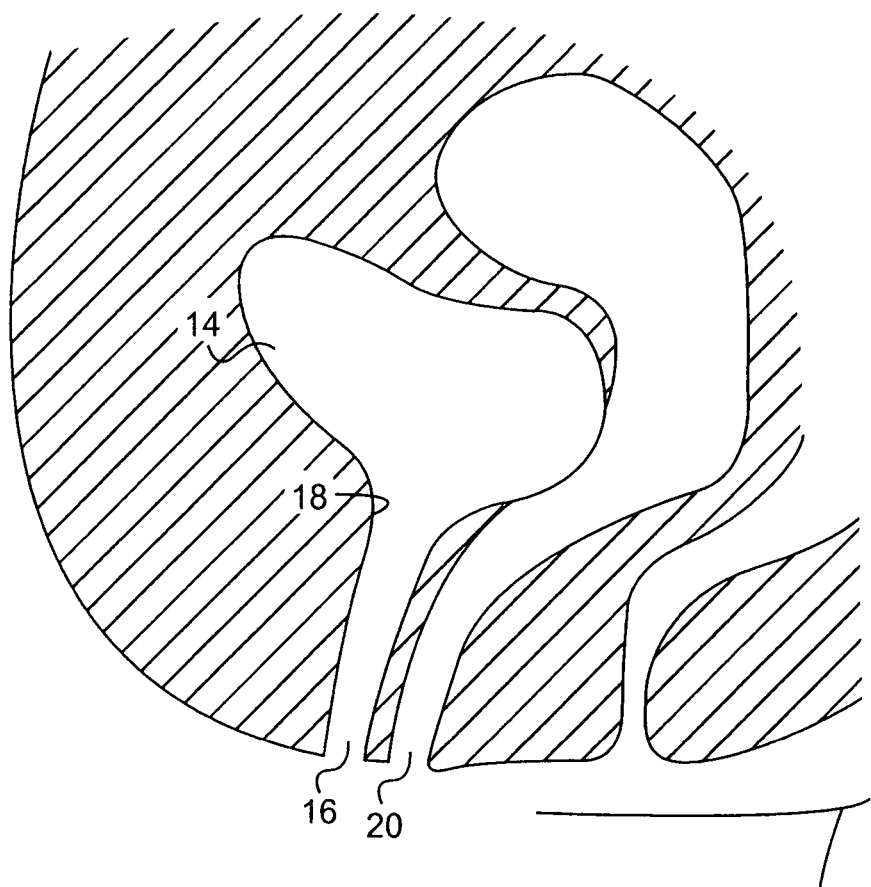
FIG. 1 shows a schematic view of the female urinary system.
Figure 2:
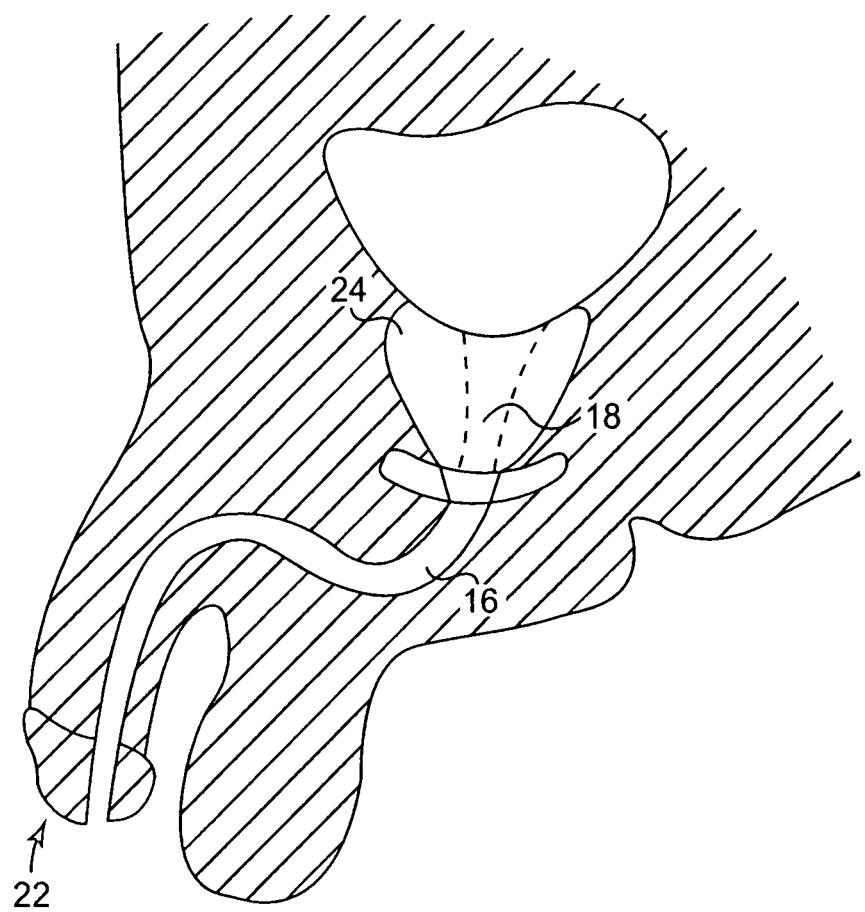
FIG. 2 is a schematic view of the male urinary system.
Figure 3:
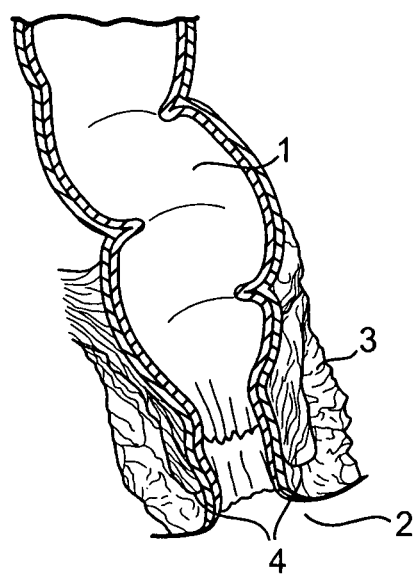
FIG. 3 is a schematic view of the anatomy of the anus and rectum.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

One aspect of the present invention is a method of treating urinary incontinence in males or females. In an embodiment, the method uses strips of mesh in strategically located positions to pull up tissue and muscle so as to re-establish the original anatomical structure. One or more strips are placed adjacent the urethra but not underneath the urethra. The mesh strips placed adjacent to the urethra provide support for the urethra.

Figure 4:
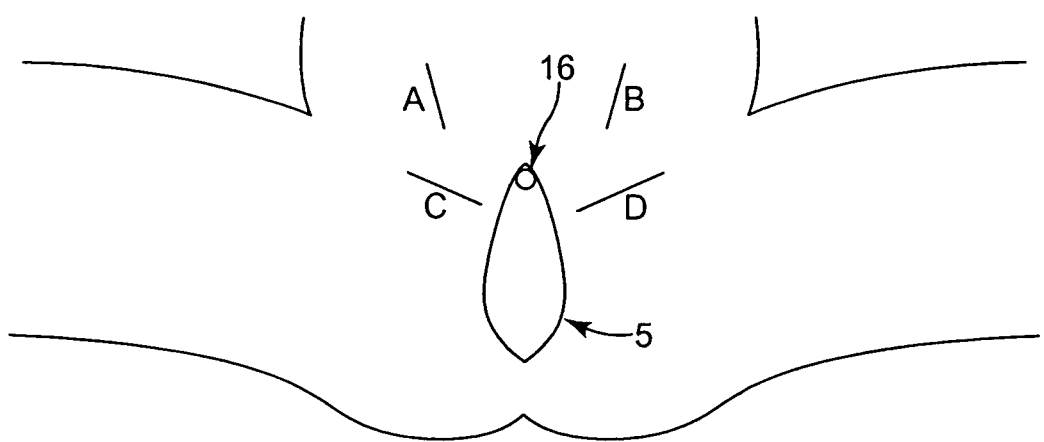
FIG. 4 shows an embodiment of the method of the present invention for treating urinary incontinence.

An embodiment of the present method for treating urinary incontinence is seen in FIG. 4. As seen in FIG. 4, the mesh strips A-D can be placed via a single vaginal 5 or perineal incision (e.g. males), followed by pushing the mesh into the appropriate anatomical position to support the urethra 16, with no need for exit incisions. The approach may be varied by the clinician in order to allow a retropubic approach where the mesh strips are in the form of a U-shape. For additional support, 1-2 additional mesh strips may be implanted. In another embodiment, mesh strips A and B can be used alone.

The present invention also encompasses mesh strips sized and shaped for practicing the present invention. Such mesh strips may optionally comprise anchors at one end in order to assist in dilating the tissue to place the present strips, as well as anchoring the mesh into the tissue as desired. In a further embodiment, the present invention encompasses such strips having anchors at both ends, such that the anchors encourage pulling the tissue and/or muscle into its desired location. In a further embodiment, the present invention encompasses a method of treating incontinence using a combination of placing mesh strips adjacent the urethra along with injection of sclerosing substances.

In yet another embodiment, the mesh strips are spring-like stents that shrink after deployment to pull in and tighten surrounding tissues.

Figure 5:
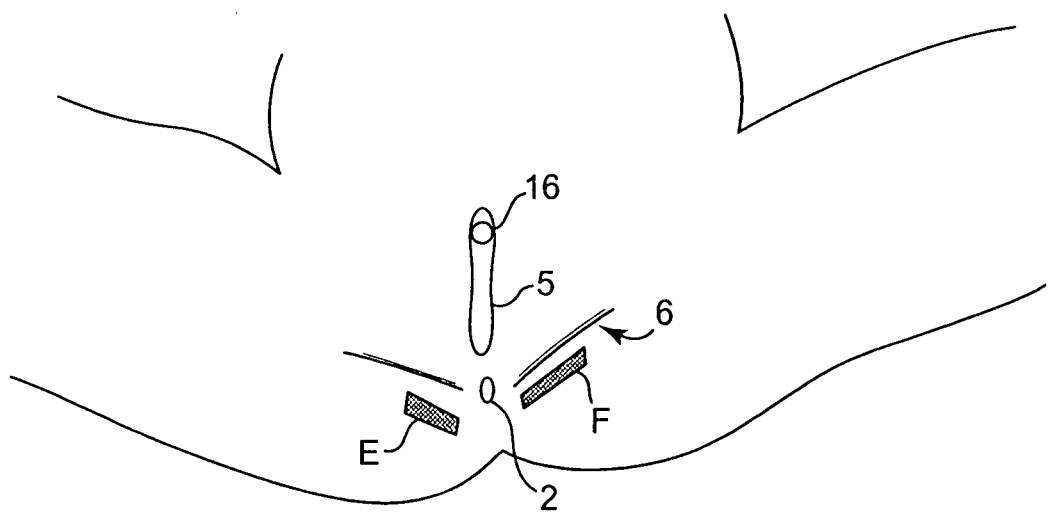
FIG. 5 shows an embodiment of the method of the present invention for treating fecal incontinence.

Another aspect of the present invention is a method of treating fecal incontinence in males or females. In an embodiment illustrated in FIG. 5, the method uses strips of mesh in strategically located positions to pull up tissue and muscle so as to re-establish the original anatomical structure. One or more strips are placed above and/or below the levator ani muscles 6 to provide support for the levator muscles and to prevent levator ballooning. As seen in FIG. 5, mesh strips E and F are placed to support the levator ani muscles 6.

In a related embodiment, the mesh strips of the present invention are pulled with sufficient tension and anchored in tissue so as to correct the anorectal angle to treat fecal incontinence. A single incision can be made adjacent the anus and the levator ani muscles on either side of the patient. Following such incision, the mesh strips are inserted with a push type introducer. The mesh strips are anchored by, for example, the inclusion of anchor structures on one or both ends of the mesh strips. However, the mesh implants may be inserted and fixed without anchors, using the fixation characteristics of the mesh material.

The present invention advantageously allows for single incision mesh strip placement to support the urethra or rectum, with no risk of mesh implant-induced erosions around the urethra or rectum. The minimal number of incisions also reduces morbidity.

U.S. Pat. Nos. 6,911,003, 6,612,977, and 6,802,807 disclose various methods and devices for treating incontinence and are herein incorporated by reference in their entirety. Other related implants and implant tools are illustrated in U.S. Patent Publication 2002/0161382 and 2004/0039453, which are herein incorporated by reference in their entirety.

Likewise, *Perineal puborectalis sling operation for fecal incontinence: preliminary report*, Dis. Colon Rectum., 2004 November; 47(11), 1982-1989, by Yamana et al, is incorporated by reference in its entirety.

In a related embodiment, the strip meshes of FIGS. 5 and 6 can be placed alongside the levator ani muscles, and/or adjacent or over the puborectalis sling muscle, to lift up the levator ani muscle(s) where there has been a pulling away (or tearing away from) of the puborectalis (PB) sling muscle or levator ani muscle away from the pubic bone. The strip mesh (or sling) can be placed in an upward fashion longitudinally along a levator ani muscle (or PB) to lift it back up to its original location where levator muscle or perineal descent has occurred. This can be done perineally (male/female) or transvaginally and with one incision or a puncture in the pelvic area Numerous modifications and variations of the present invention are possible in light of the above teachings. Further, these techniques and devices are described as treatment for urinary incontinence. Their use in treating organ prolapse and other urologic conditions is also contemplated. It is therefore to be understood that within the scope of the appended claims, the invention may be practiced otherwise than as specifically described herein.

The invention claimed is:

1. A method of treating fecal incontinence or levator ballooning, comprising:
    making a perineal incision in a patient;
    placing through the perineal incision a first strip of spring-like mesh material proximate, generally parallel to, and longitudinally along the levator ani muscles to support the levator ani muscles, wherein the first strip of mesh is not placed in a position directly abutting the levator ani muscles; and
    placing a second strip of spring-like mesh material proximate, generally parallel to, and longitudinally along the levator ani muscles to support the levator ani muscles, wherein the second strip of mesh is not placed in a position directly abutting the levator ani muscles such that the second strip of mesh is physically separate from and not connected to the first strip of mesh or any distal mesh materials.

2. The method of claim 1, further including third and fourth strips of spring-like mesh material placed in different locations proximate the levator ani muscles, wherein the third and fourth strips of mesh are not placed in a position directly abutting the levator ani muscles.

3. The method of claim 1, wherein at least one of the first or second strips of mesh material is made from a bioabsorbable material.

4. The method of claim 1, further comprising anchoring at least one of the first or second strips of mesh material in a position proximate the levator ani muscles.

5. A method of treating fecal incontinence or levator ballooning, comprising:
    making a perineal incision in a patient;
    introducing a tool through the perineal incision along a tissue path toward the levator ani muscles of a patient;
    placing through the perineal incision a first strip of spring-like mesh material proximate, generally parallel to, and longitudinally along the levator ani muscles to support the levator ani muscles, wherein the first strip of mesh is not placed in a position directly abutting the levator ani muscles;
    placing through the perineal incision a second strip of spring-like mesh material proximate, generally parallel to, and longitudinally along the levator ani muscles to support the levator ani muscles, wherein the second strip of mesh is not placed in a position directly abutting the levator ani muscles, wherein the second strip of mesh is physically separate from and not connected to the first strip of mesh or any distal mesh materials.

6. The method of claim 5, further including third and fourth strips of spring-like mesh material placed in different locations proximate the levator ani muscles, wherein the third and fourth strips of mesh are not placed in a position directly abutting the levator ani muscles.

7. The method of claim 5, wherein at least one of the first or second strips of mesh material is made from a bioabsorbable material.

8. The method of claim 5, further comprising anchoring at least one of the first or second strips of mesh material in a position proximate the levator ani muscles.

* * * * *